(12) United States Patent
Weickert et al.

(10) Patent No.: US 9,714,967 B1
(45) Date of Patent: *Jul. 25, 2017

(54) ELECTROSTATIC DUST AND DEBRIS SENSOR FOR AN ENGINE

(71) Applicant: General Electric Company, Schenectady, NY (US)

(72) Inventors: John David Weickert, Fairfield, OH (US); Gregory Griffin, Mason, OH (US); James R. Noel, Beverly, MA (US); Charles Rickards, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 18 days.

This patent is subject to a terminal disclaimer.

(21) Appl. No.: 15/007,289

(22) Filed: Jan. 27, 2016

(51) Int. Cl.
| | |
|---|---|
| *G01N 27/60* | (2006.01) |
| *G01R 29/12* | (2006.01) |
| *G01N 27/61* | (2006.01) |
| *G01R 29/24* | (2006.01) |
| *G01M 15/14* | (2006.01) |

(52) U.S. Cl.
CPC ............ *G01R 29/12* (2013.01); *G01N 27/60* (2013.01); *G01N 27/61* (2013.01); *G01R 29/24* (2013.01); *G01M 15/14* (2013.01)

(58) Field of Classification Search
CPC ........ G01N 27/61; G01N 27/60; G01N 27/24; G01M 15/14; G01R 29/12; G01R 29/24
USPC .................................................. 324/456, 457
See application file for complete search history.

(56) References Cited

U.S. PATENT DOCUMENTS

| | | | |
|---|---|---|---|
| 3,917,432 | A | 11/1975 | Feuerstein |
| 4,249,131 | A | 2/1981 | Owen |
| 4,531,402 | A | 7/1985 | Reif et al. |

(Continued)

FOREIGN PATENT DOCUMENTS

| | | |
|---|---|---|
| GB | 2335745 A | 9/1999 |
| GB | 2482480 A | 2/2012 |

(Continued)

OTHER PUBLICATIONS

US Non-Final OA issued in connection with Related U.S. Appl. No. 15/007,282 on Nov. 10, 2016.

(Continued)

*Primary Examiner* — Amy He
(74) *Attorney, Agent, or Firm* — Pamela A. Kachur

(57) ABSTRACT

The present disclosure is directed to an integrated electrostatic sensor for an engine. The sensor includes an outer housing having a body with a first end and a second end. The first end is configured for securing the sensor to the engine and includes a sensing face. The sensor also includes an electrode configured within the housing adjacent to the sensing face and an amplifier configured with the electrode. The electrode contains a plurality of electrons configured to move as charged particles flow past the sensing face. Thus, the amplifier is configured to detect a particulate level as a function of the electron movement. The electrostatic sensor also includes a circuit board configured within the housing and electrically coupled to the amplifier. As such, the circuit board is configured to send one or more signals to a controller of the engine indicative of the particulate level.

17 Claims, 6 Drawing Sheets

(56) References Cited

U.S. PATENT DOCUMENTS

| | | | |
|---|---|---|---|
| 4,531,486 A | 7/1985 | Reif et al. | |
| 4,888,948 A | 12/1989 | Fisher | |
| 5,070,722 A | 12/1991 | Hawman | |
| 5,602,543 A | 2/1997 | Prata | |
| 6,668,655 B2 | 12/2003 | Harrold | |
| 7,275,415 B2 | 10/2007 | Rhodes | |
| 7,419,532 B2 | 9/2008 | Sellers | |
| 7,518,098 B2 | 4/2009 | Mack | |
| 7,549,317 B2 | 6/2009 | Rhodes | |
| 7,628,007 B2* | 12/2009 | Kittelson | F01N 11/007 60/274 |
| 7,895,818 B2 | 3/2011 | Snell | |
| 8,037,738 B2 | 10/2011 | Boehler et al. | |
| 8,256,277 B2 | 9/2012 | Khibnik | |
| 8,424,279 B2 | 4/2013 | Rajamani | |
| 8,459,103 B2 | 6/2013 | Khibnik | |
| 8,761,490 B2 | 6/2014 | Scheid | |
| 8,941,396 B2 | 1/2015 | Cok | |
| 9,010,198 B2 | 4/2015 | Rajamani | |
| 9,074,868 B2 | 7/2015 | Bendall | |
| 2006/0156791 A1* | 7/2006 | Tikkanen | G01N 27/62 73/23.31 |
| 2009/0045967 A1 | 2/2009 | Bandholz | |
| 2010/0287907 A1 | 11/2010 | Agrawal et al. | |
| 2010/0288034 A1 | 11/2010 | Agrawal et al. | |
| 2010/0292905 A1 | 11/2010 | Agrawal et al. | |
| 2010/0313639 A1 | 12/2010 | Khibnik | |
| 2011/0062973 A1 | 3/2011 | Paterson | |
| 2011/0079015 A1 | 4/2011 | Geis et al. | |
| 2011/0179763 A1 | 7/2011 | Rajamani | |
| 2011/0192211 A1* | 8/2011 | Yokoi | G01N 27/4163 73/1.06 |
| 2012/0068862 A1 | 3/2012 | Tillotson | |
| 2012/0324987 A1 | 12/2012 | Khibnik | |
| 2013/0025348 A1 | 1/2013 | Rajamani | |
| 2013/0058419 A1 | 3/2013 | Ye | |
| 2013/0180271 A1 | 7/2013 | Kuczynski | |
| 2013/0193978 A1 | 8/2013 | Woolley | |
| 2013/0220004 A1 | 8/2013 | Epstein et al. | |
| 2014/0331743 A1 | 11/2014 | Kwon | |

FOREIGN PATENT DOCUMENTS

| | | |
|---|---|---|
| GB | 2842480 A | 2/2012 |
| GB | 2496903 A | 5/2013 |
| WO | WO2015/034513 A1 | 3/2015 |

OTHER PUBLICATIONS

US Notice of Allowance issued in connection with Related U.S. Appl. No. 15/375,882 on Feb. 1, 2017.
GE Related Case Form
U.S. Appl. No. 15/007,282, filed Jan. 27, 2016, John David Weickert et al.
U.S. Appl. No. 15/375,882, filed Dec. 12, 2016, John David Weickert et al.

* cited by examiner

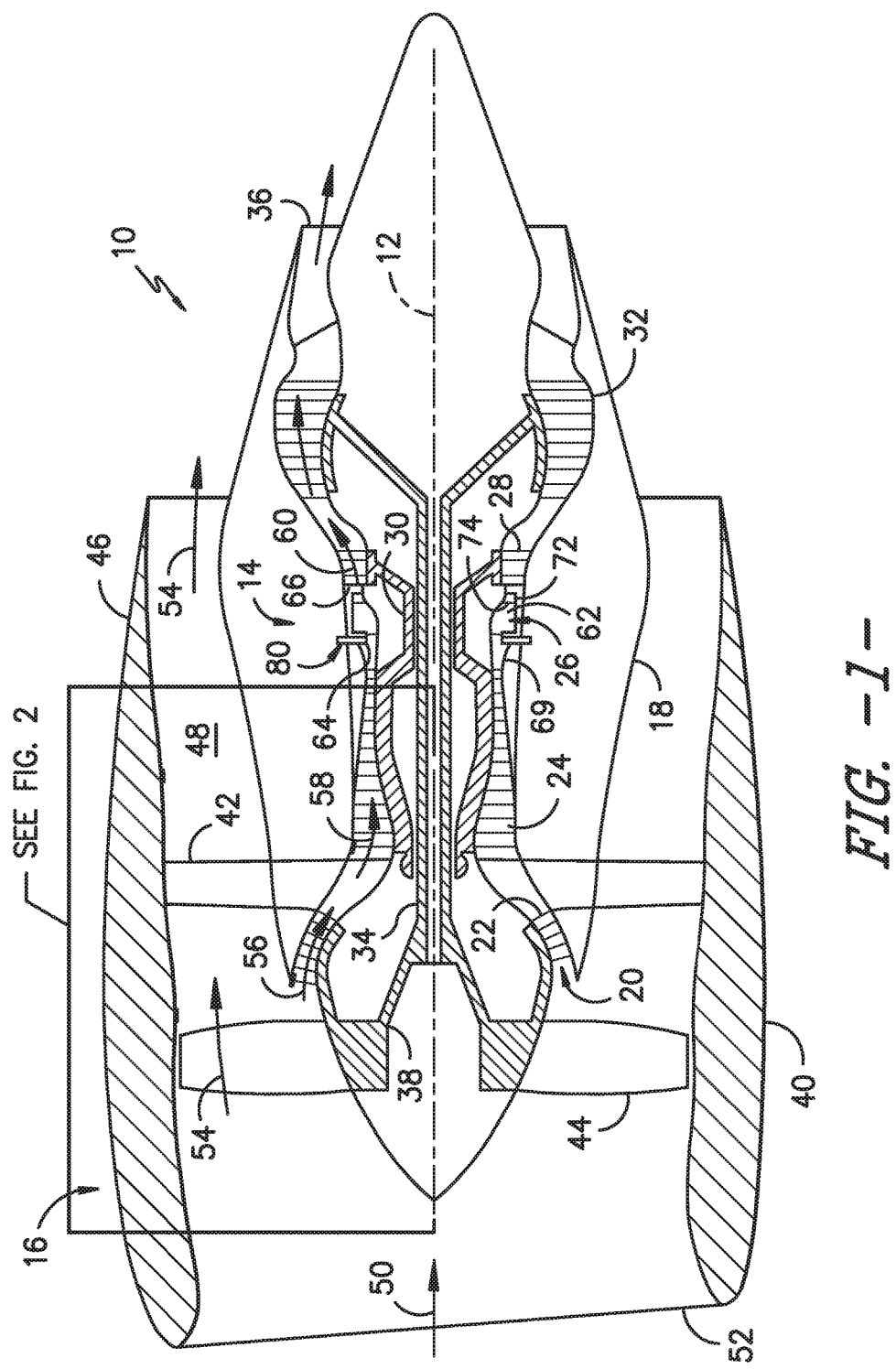
FIG. -1-

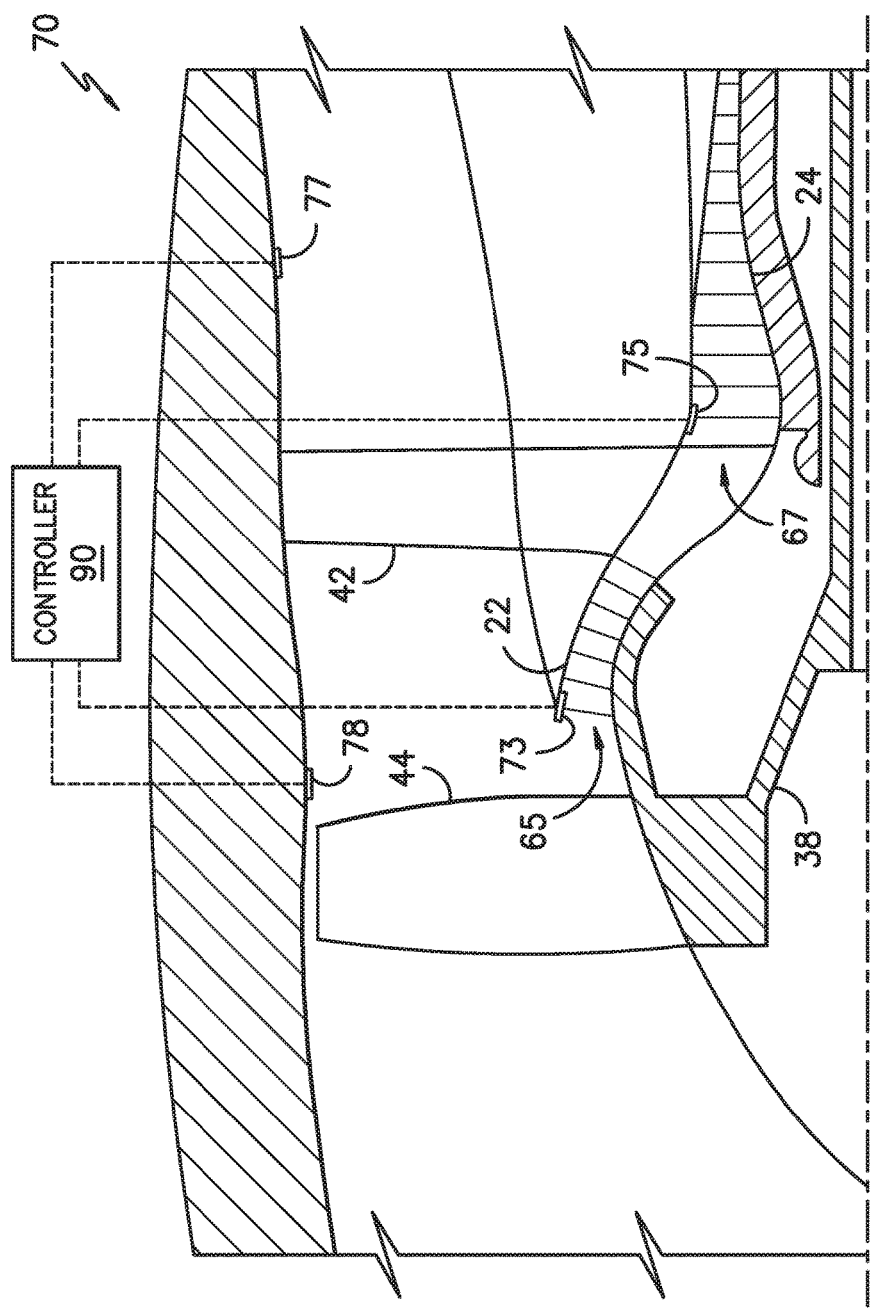

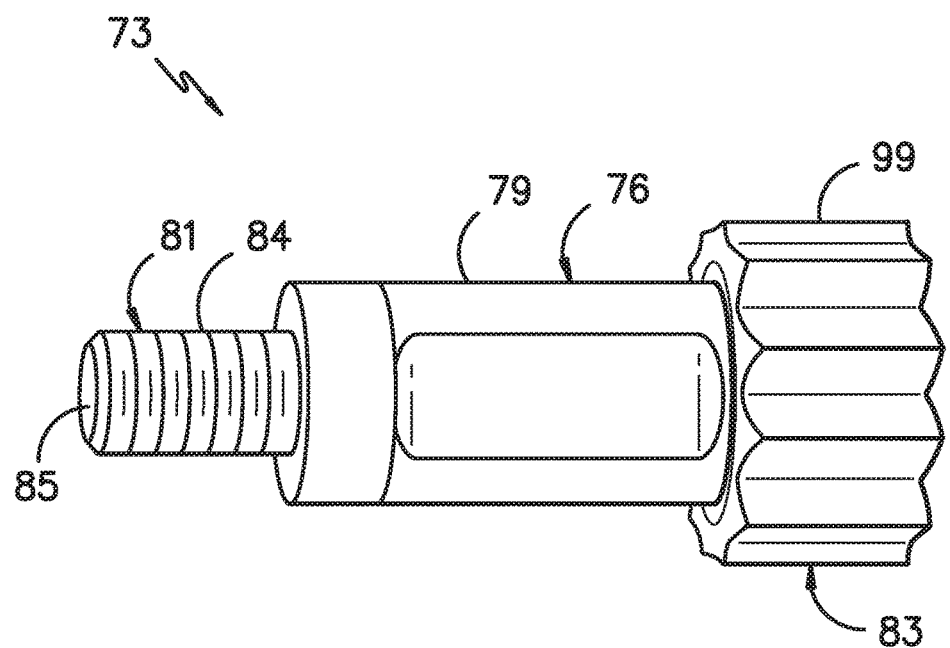
FIG. -3-
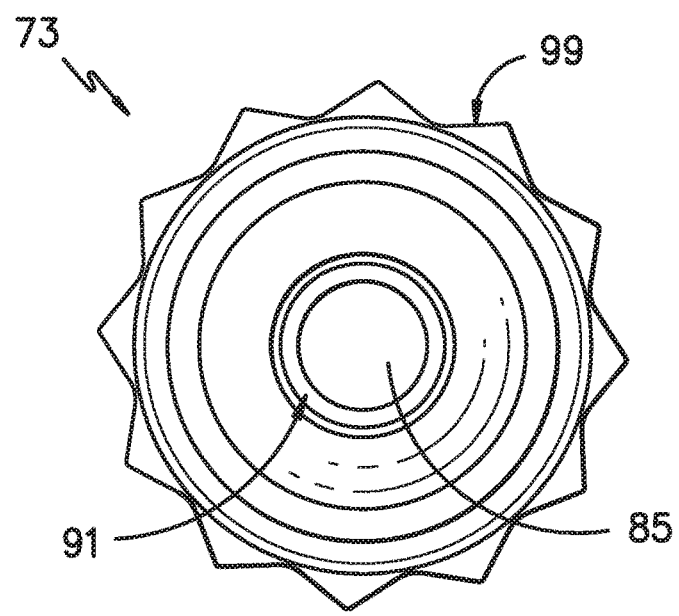
FIG. -4-

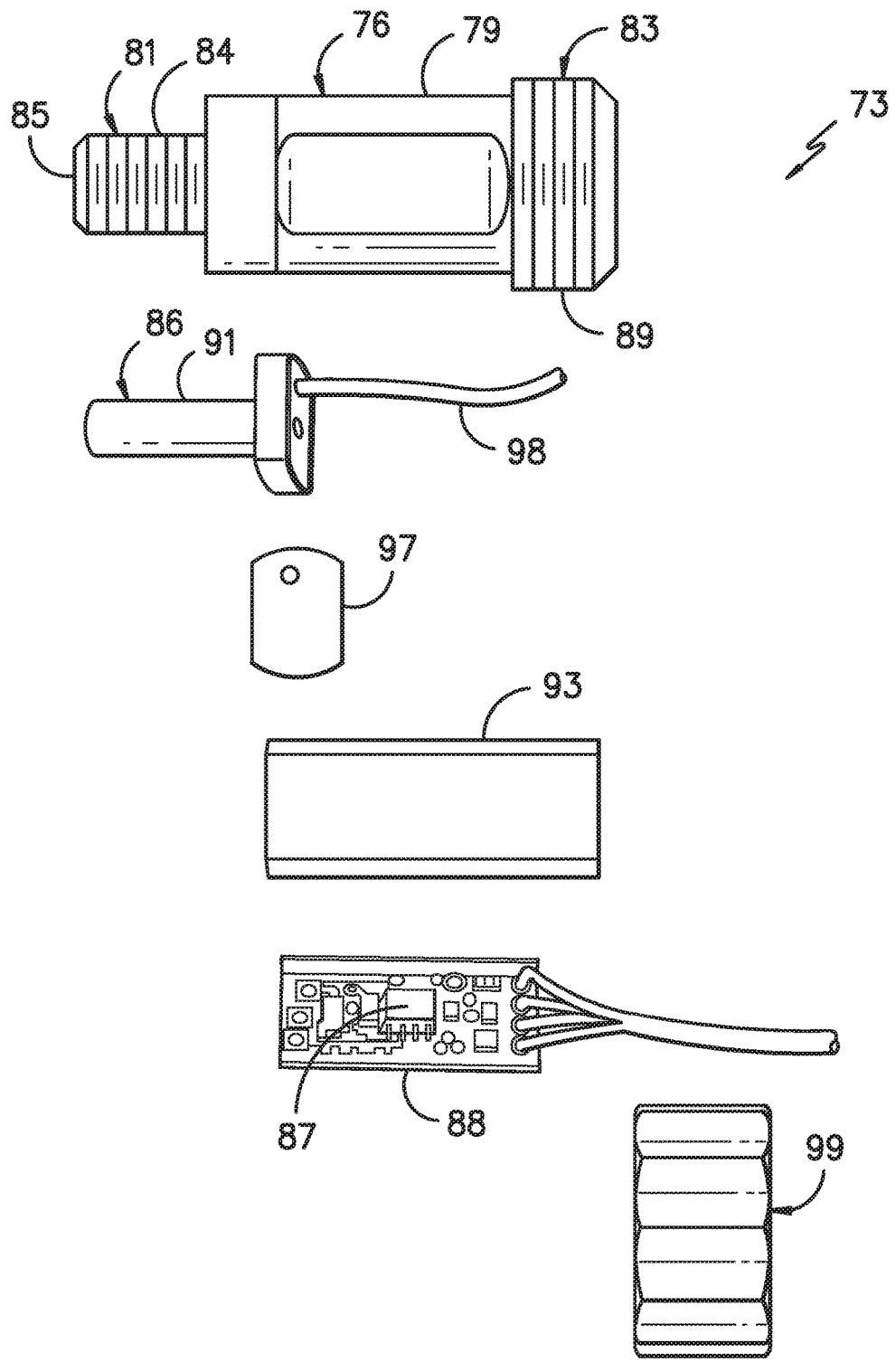
FIG. -5-

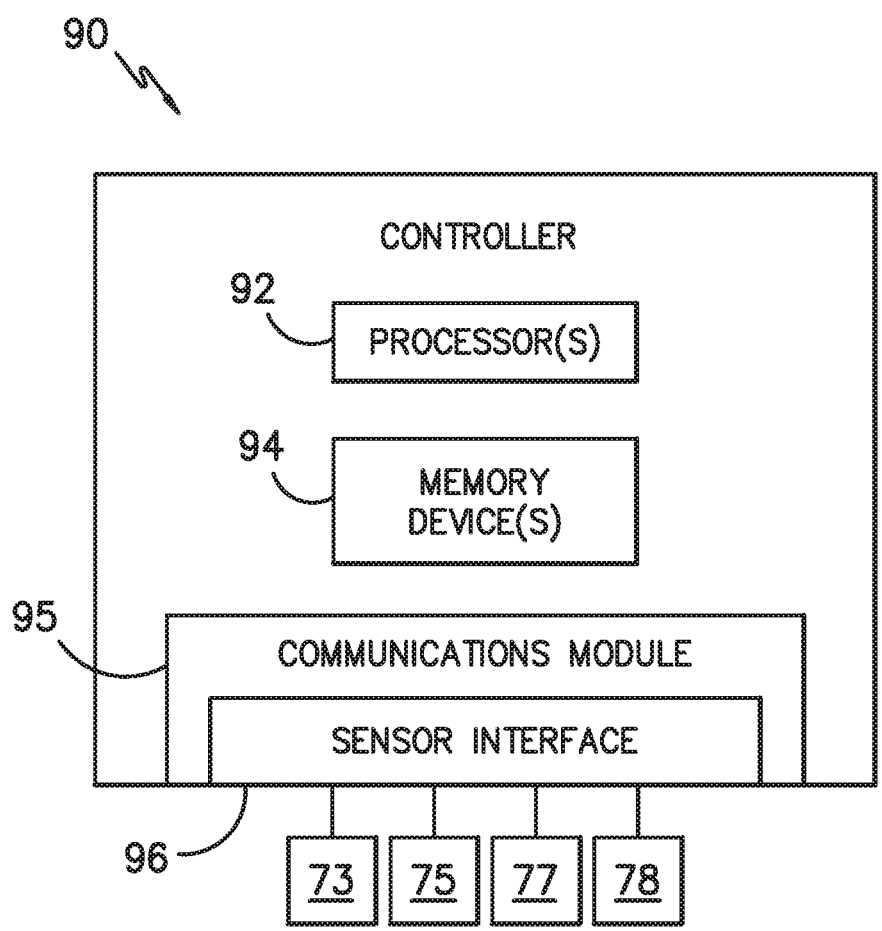
FIG. -6-

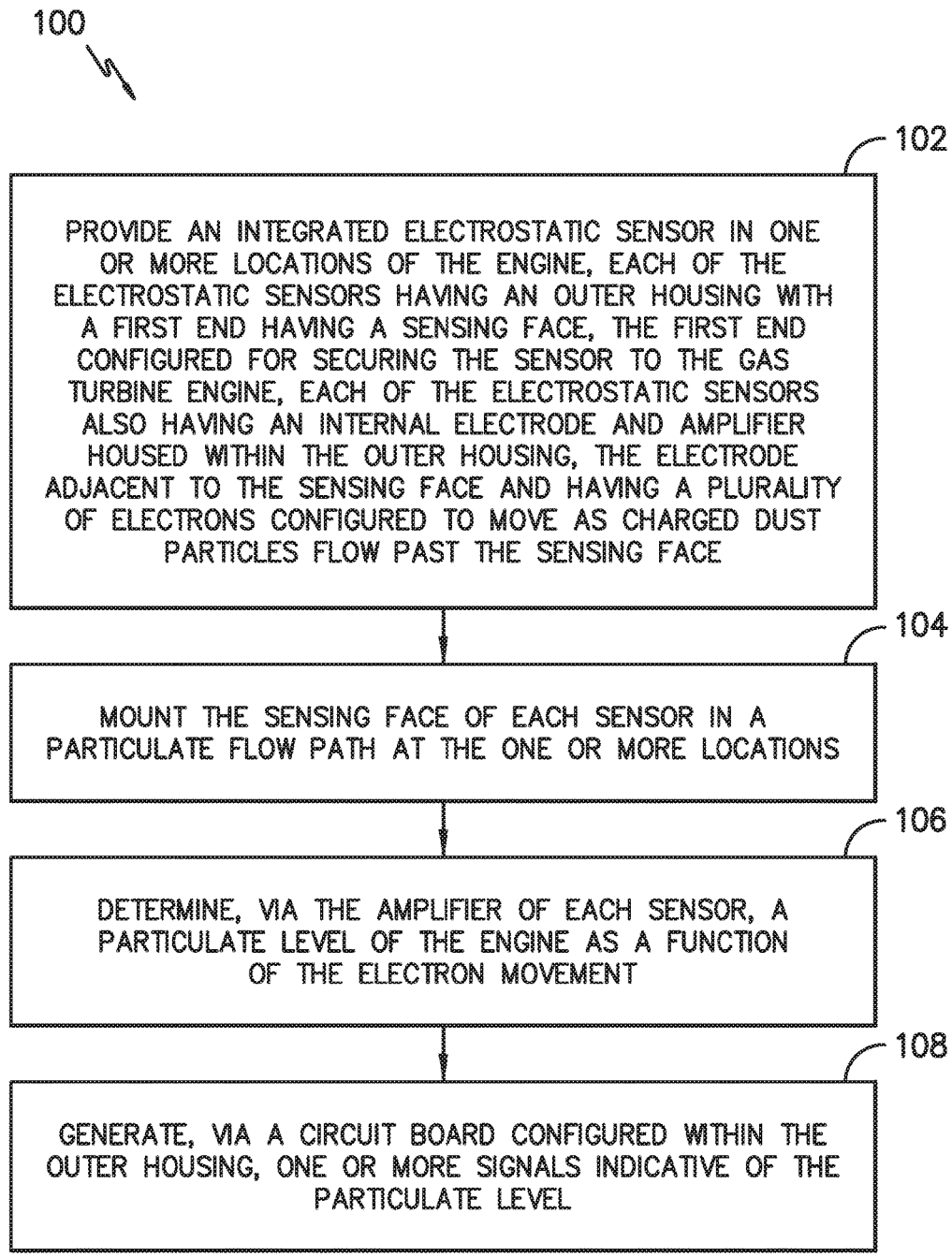
FIG. -7-

ELECTROSTATIC DUST AND DEBRIS SENSOR FOR AN ENGINE

FIELD OF THE INVENTION

The present subject matter relates generally to dust and debris sensors, and more particularly, to electrostatic dust and debris sensors for engines, such as gas turbine engines.

BACKGROUND OF THE INVENTION

A gas turbine engine generally includes, in serial flow order, a compressor section, a combustion section, a turbine section and an exhaust section. In operation, air enters an inlet of the compressor section where one or more axial or centrifugal compressors progressively compress the air until it reaches the combustion section. Fuel is mixed with the compressed air and burned within the combustion section to provide combustion gases. The combustion gases are routed from the combustion section through a hot gas path defined within the turbine section and then exhausted from the turbine section via the exhaust section.

In particular configurations, the turbine section includes, in serial flow order, a high pressure (HP) turbine and a low pressure (LP) turbine. The HP turbine and the LP turbine each include various rotatable turbine components such as turbine rotor blades, rotor disks and retainers, and various stationary turbine components such as stator vanes or nozzles, turbine shrouds, and engine frames. The rotatable and stationary turbine components at least partially define the hot gas path through the turbine section. As the combustion gases flow through the hot gas path, thermal energy is transferred from the combustion gases to the rotatable and stationary turbine components.

Such gas turbine engines are commonly employed in an aircraft. During operation of the aircraft, the engine environmental particulate and dust ingestion level is a key input to the analytics process, resulting in specific engine-by-engine action. Current particulate level data is provided by ground-based and/or remote sensing systems. Such data has temporal and special variations as well as error, thereby making accurate assessment of engine conditions at takeoff and climb of the aircraft particularly difficult. Further, the electronics of such sensor systems are typically connected to the individual sensors via a plurality of cables and connectors. Thus, any motion or vibration of the cabling can produce more charge than the dust or debris particles passing the sensor face, thereby resulting in a poor signal-to-noise ratio. Further, conventional systems can experience issues due to the triboelectric and piezoelectric effects of the cables and connectors.

Accordingly, the present disclosure is directed to an improved sensor system that addresses the aforementioned issues. More specifically, the present disclosure is directed to a sensor system that includes one or more improved electrostatic sensors having integrated electronics that more accurately detects dust particles and/or debris within an engine such as the gas turbine engine described above.

BRIEF DESCRIPTION OF THE INVENTION

Aspects and advantages of the invention will be set forth in part in the following description, or may be obvious from the description, or may be learned through practice of the invention.

In one aspect, the present disclosure is directed to an integrated electrostatic sensor for detecting dust and/or debris in an engine, such as an aircraft engine. The sensor includes an outer housing having a body with a first end and a second end. The first end is configured for securing the sensor to the engine and includes a sensing face. The sensor also includes an electrode configured within the housing adjacent to the sensing face and an amplifier configured with the electrode. The electrode contains a plurality of electrons configured to move as charged particles within the engine flow past the sensing face. Thus, the amplifier is configured to detect a particulate level of the engine as a function of the electron movement. The electrostatic sensor also includes a circuit board configured within the outer housing and electrically coupled to the amplifier. As such, the circuit board is configured to send one or more signals to a controller of the engine indicative of the particulate level.

In another aspect, the present disclosure is directed to an electrostatic sensor system for an engine. The sensor system includes one or more integrated electrostatic sensors for detecting dust and/or debris in the engine. Each of the electrostatic sensors includes an outer housing having a body with a first end and a second end. The first end is configured for securing the sensor to the engine and includes a sensing face. Each sensor also includes an electrode configured within the outer housing adjacent to the sensing face and an amplifier configured with the electrode. The electrode contains a plurality of electrons configured to move as charged dust or debris particles within the engine flow past the sensing face. Thus, the amplifier is configured to detect a particulate level as a function of the electron movement. Each of the sensors also includes a circuit board configured within the outer housing and electrically coupled to the amplifier. Thus, the sensor system also includes a controller electrically coupled to the circuit board so as to receive one or more signals generated thereby that are indicative of the particulate level. It should be understood that the sensor system may be further configured with any of the additional features as described herein.

In yet another aspect, the present disclosure is directed to a method for detecting dust or debris in an engine, e.g. in an aircraft engine. The method includes providing an integrated electrostatic sensor in one or more locations of the engine, with each of the electrostatic sensors including an outer housing having a first end and second end. The first end of the outer housing is configured for securing the sensor to the engine and includes a sensing face. Further, each of the electrostatic sensors includes an internal electrode and amplifier housed within the outer housing. The electrode is adjacent to the sensing face and has a plurality of electrons configured to move as charged particles within the engine flow past the sensing face. Thus, the method also includes mounting the sensing face of each sensor in a particulate flow path at the one or more locations. In addition, the method includes determining, via the amplifier of each sensor, a particulate level of the engine as a function of the electron movement. The method also includes generating, via a circuit board configured within the outer housing, one or more signals indicative of the particulate level. It should be understood that the method may further include any additional steps and/or features as described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a schematic cross-sectional view of one embodiment of a gas turbine engine according to the present disclosure;

FIG. 2 illustrates a schematic diagram of one embodiment of a sensor system for detecting dust or debris in an engine according to the present disclosure;

FIG. 3 illustrates a perspective view of one embodiment of an electrostatic sensor for detecting dust or debris in an engine according to the present disclosure;

FIG. 4 illustrates a bottom view of one embodiment of an electrostatic sensor for detecting dust or debris in an engine according to the present disclosure, particularly illustrating the sensing face of the sensor;

FIG. 5 illustrates perspective views of the various components of the electrostatic sensor for detecting dust or debris in an engine according to the present disclosure;

FIG. 6 illustrates a block diagram of one embodiment of suitable components that may be included in a controller of an engine according to the present disclosure; and FIG. 7 illustrates a flow diagram of one embodiment of method for detecting dust or debris in an engine according to the present disclosure.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "first", "second", and "third" may be used interchangeably to distinguish one component from another and are not intended to signify location or importance of the individual components.

The terms "upstream" and "downstream" refer to the relative direction with respect to fluid flow in a fluid pathway. For example, "upstream" refers to the direction from which the fluid flows, and "downstream" refers to the direction to which the fluid flows.

Generally, the present disclosure is directed to an electrostatic sensor system and methods for detecting dust, debris and/or other airborne particulates in an engine, e.g. an aircraft gas turbine engine. Further, it should be understood that the electrostatic sensor system and related methods are also suitable for any other type of engine, including but not limited to an industrial engine, a power generation engine, a land-based engine, a marine engine, or similar. More specifically, in certain embodiment, the electrostatic sensor system may include a controller electrically coupled with one or more electrostatic sensors. Each of the electrostatic sensors includes an outer housing having a first end configured for securing the sensor to the engine and having a sensing face. The sensor also includes an internal electrode configured within the outer housing adjacent to the sensing face and an amplifier configured with the electrode. The electrode contains a plurality of electrons configured to move as charged particles flow past the sensing face. Thus, the amplifier is configured to detect a particulate level as a function of electron movement. The electrostatic sensor also includes a circuit board configured within the outer housing and electrically coupled to the amplifier. Thus, the circuit board is configured to send the one or more signals to a controller of the engine indicative of the particulate level.

Thus, the outer housing and electronics configuration minimize the distance between the sensor input and the electrode, thereby increasing sensitivity of the sensor. As such, the present disclosure provides various advantages not present in the prior art. For example, the electrostatic sensors of the present disclosure provide more accurate particulate (e.g. dust, debris, or similar) detection in engines that is robust and reliable. Further, since the electronics are integrated within the sensor, the present design requires less maintenance and suffers from fewer operational issues over prior art designs. Moreover, the amplifier low leakage current facilitates DC coupling of the amplifier, which allows low frequency changes in particulate levels to be captured. In addition, the high input impedance of the electrode improves the sensor sensitivity to small changes in charge in the sensing face. Further, the high input impedance of the electrode also improves the low frequency response of the sensor by preventing sensed electrons from leaking away such that an output signal cannot be produced. Thus, the electrostatic sensor of the present disclosure is capable of detecting from about one (1) part in seven (7) million by mass of particles. Moreover, electrostatic sensors of the present disclosure can provide ice detection, as well as volcanic ash and/or other damaging ingested particulate detection in addition to dust.

Referring now to the drawings, FIG. 1 illustrates a schematic cross-sectional view of one embodiment of a gas turbine engine 10 (high-bypass type) according to the present disclosure. More specifically, the gas turbine engine 10 may include an aircraft engine, e.g. for an airplane, helicopter, or similar. As shown, the gas turbine engine 10 has an axial longitudinal centerline axis 12 therethrough for reference purposes. Further, as shown, the gas turbine engine 10 preferably includes a core gas turbine engine generally identified by numeral 14 and a fan section 16 positioned upstream thereof. The core engine 14 typically includes a generally tubular outer casing 18 that defines an annular inlet 20. The outer casing 18 further encloses and supports a booster 22 for raising the pressure of the air that enters core engine 14 to a first pressure level. A high pressure, multi-stage, axial-flow compressor 24 receives pressurized air from the booster 22 and further increases the pressure of the air. The compressor 24 includes rotating blades and stationary vanes that have the function of directing and compressing air within the turbine engine 10. The pressurized air flows to a combustor 26, where fuel is injected into the pressurized air stream and ignited to raise the temperature and energy level of the pressurized air. The high energy combustion products flow from the combustor 26 to a first (high pressure) turbine 28 for driving the high pressure compressor 24 through a first (high pressure) drive shaft 30, and then to a second (low pressure) turbine 32 for driving the booster 22 and the fan section 16 through a second (low pressure) drive shaft 34 that is coaxial with the first drive shaft 30. After driving each of the turbines 28 and 32, the combustion products leave the core engine 14 through an exhaust nozzle 36 to provide at least a portion of the jet propulsive thrust of the engine 10.

The fan section 16 includes a rotatable, axial-flow fan rotor 38 that is surrounded by an annular fan casing 40. It will be appreciated that fan casing 40 is supported from the core engine 14 by a plurality of substantially radially-extending, circumferentially-spaced outlet guide vanes 42. In this way, the fan casing 40 encloses the fan rotor 38 and the fan rotor blades 44. The downstream section 46 of the fan casing 40 extends over an outer portion of the core engine 14 to define a secondary, or bypass, airflow conduit 48 that provides additional jet propulsive thrust.

From a flow standpoint, it will be appreciated that an initial airflow, represented by arrow 50, enters the gas turbine engine 10 through an inlet 52 to the fan casing 40. The airflow passes through the fan blades 44 and splits into a first air flow (represented by arrow 54) that moves through the conduit 48 and a second air flow (represented by arrow 56) which enters the booster 22.

The pressure of the second compressed airflow 56 is increased and enters the high pressure compressor 24, as represented by arrow 58. After mixing with fuel and being combusted in the combustor 26, the combustion products 60 exit the combustor 26 and flow through the first turbine 28. The combustion products 60 then flow through the second turbine 32 and exit the exhaust nozzle 36 to provide at least a portion of the thrust for the gas turbine engine 10.

Still referring to FIG. 1, the combustor 26 includes an annular combustion chamber 62 that is coaxial with the longitudinal centerline axis 12, as well as an inlet 64 and an outlet 66. As noted above, the combustor 26 receives an annular stream of pressurized air from a high pressure compressor discharge outlet 69. A portion of this compressor discharge air flows into a mixer (not shown). Fuel is injected from a fuel nozzle 80 to mix with the air and form a fuel-air mixture that is provided to the combustion chamber 62 for combustion. Ignition of the fuel-air mixture is accomplished by a suitable igniter, and the resulting combustion gases 60 flow in an axial direction toward and into an annular, first stage turbine nozzle 72. The nozzle 72 is defined by an annular flow channel that includes a plurality of radially-extending, circumferentially-spaced nozzle vanes 74 that turn the gases so that they flow angularly and impinge upon the first stage turbine blades of the first turbine 28. As shown in FIG. 1, the first turbine 28 preferably rotates the high-pressure compressor 24 via the first drive shaft 30, whereas the low-pressure turbine 32 preferably drives the booster 22 and the fan rotor 38 via the second drive shaft 34.

The combustion chamber 62 is housed within the engine outer casing 18 and fuel is supplied into the combustion chamber 62 by one or more fuel nozzles 80. More specifically, liquid fuel is transported through one or more passageways or conduits within a stem of the fuel nozzle 80.

During operation, dust and other types of aerosol particulates are ingested by the gas turbine engine 10, e.g. from air entering the inlet 52. Dust and aerosol particulate accumulation is a key input for engine analytics as these levels are important in evaluating engine service time, wear and tear, and/or other maintenance schedules. Thus, the present disclosure is directed to an improved electrostatic sensor system 70 (FIG. 2) and method 100 (FIG. 7) for detecting dust and/or debris in the gas turbine engine 10, such as those described herein. More specifically, as shown in FIG. 2, the sensor system 70 includes one or more electrostatic sensors 73, 75, 77, 78 communicatively coupled to a controller 90. Each of the electrostatic sensors 73, 75, 77, 78 are configured in a similar manner, therefore, FIGS. 3-5 illustrate various views of one of the electrostatic sensors 73 for illustrative purposes only. For example, FIG. 3 illustrates a perspective view of the electrostatic sensor 73; FIG. 4 illustrates a bottom view of the electrostatic sensor 73 as viewed from the sensing face 85; and FIG. 5 illustrates perspective views of the various components of the electrostatic sensor 73.

As shown in FIGS. 3 and 5, the electrostatic sensor 73 defines an outer housing 76 or casing that includes a body 79 having a first end 81 and a second end 83. Further, as shown, the first end 81 of the sensor 73 defines a sensing face 85. In addition, the first end 81 is configured to be mounted or otherwise secured to the gas turbine engine 10. For example, in certain embodiments, the body 79 of the outer housing 76 may have a predetermined shape configured to fit in an existing location of the gas turbine engine 10. More specifically, as shown in FIGS. 3-5, the predetermined shape of the body 79 of the outer housing 76 may be a generally cylindrical shape. Thus, as shown in FIG. 2, the existing location of the gas turbine engine 10 may include a borescope port (e.g. sensor 75) or a wash water port (e.g. sensor 78). In additional embodiments, the existing location of the gas turbine engine 10 may include a compressor inlet (e.g. sensor 75), a booster inlet (e.g. sensor 73), or a turbine inlet (not shown) of the gas turbine engine 10. As such, in any of the embodiments described herein, the first end 81 of the outer housing 76 may include a first threaded outer surface 84 configured for securing the sensor 73 in a mounting location of the gas turbine engine 10. It should be understood that the outer housing 76 may further be adapted to fit in any suitable location of the gas turbine engine 10 where particulate detection is desired.

Referring particularly to FIG. 5, the electrostatic sensor 73 includes an internal electrode 86 and amplifier 87 configured within the outer housing 76 adjacent to the sensing face 85. Further, the electrode 86 contains a plurality of electrons (not shown) configured to move within the electrode 86 as charged particles within the engine 10 flow past the sensing face 85. More specifically, the electrons are configured to move within the electrode 86 either towards or away from the sensing face 85 based on the charge of the passing particles. In certain embodiments, the sensor 73 may also include an electrode housing 91 configured within the outer housing 76 adjacent to the sensor face 85. As such, the electrode housing 91 is configured to house and protect the electrode 86. Accordingly, the amplifier 87 is configured to detect or measure the location of the electrons within the electrode 83 so as to indicate a particulate level of the charged particles flowing past the sensing face 79. Thus, the amplifier 87 is configured to detect a particulate level as a function of the electron movement.

As mentioned, the integrated amplifier 87 of the present disclosure is extremely sensitive and capable of more accurately detecting particulate levels of the gas turbine engine 10. More specifically, in certain embodiments, the amplifier 87 may include a leakage current of from about 1 femtoampere to about 5 femtoampere, more preferably about 3 femtoampere. Thus, the low leakage current facilitates DC coupling of the amplifier 87, which allows low frequency changes in particulate levels to be captured. Further, the amplifier 87 may have an operating temperature range of from about 100 degrees Celsius (° C.) to about 250° C., more preferably from about 150° C. to about 230° C. Moreover, the electrode 86 may have an impedance of greater than about 1 G-Ohm, for example about 10 G-Ohm. As such, the high input impedance of the electrode 86 is configured to improve the sensor sensitivity to small changes in charge in the sensing face 85. In addition, the high input impedance is also configured to improve the low frequency response of the sensor 73 by preventing sensed electrons from leaking away such that an output signal cannot be produced. Thus, the electrostatic sensor(s) 73 of the present disclosure is capable of detecting from about one (1) part in seven (7) million by mass of particles.

In additional embodiments, the electrostatic sensor(s) 73 is further configured to detect any/all airborne aerosol particulates including but not limited to ice crystals, construction debris, sand, and/or volcanic ash within the engine flowpath and alert the controller 90 in the event of such detection. Further, the electrostatic sensor(s) 73 is further configured to detect internally-generated dust and debris and alert the controller.

Referring particularly to FIG. 5, the electrostatic sensor 73 also includes an integrated circuit board 88 configured within the outer housing 76 and electrically coupled to the amplifier 87. Further, as shown, the electrode 86 may be electrically coupled to the circuit board 88 via an insulated wire 98. More specifically, as shown, the circuit board 86 may be configured adjacent to the electrode 86 and opposite the sensing face 85. In additional embodiments, the circuit board 88 may be located at any suitable location within the outer housing 76 of the sensor 73. Further, the circuit board 88 as described herein may include any suitable circuit board that mechanically supports and electrically connects the electronic components of the sensor(s) 73. More specifically, certain circuit boards of the present disclosure may include conductive tracks, pads, and/or other features etched from metal, such as copper, sheets that are laminated onto a non-conductive substrate. Further, the circuit board 88 of the present disclosure may be single-sided, double-sided, or multi-layered. Thus, the circuit board 88 as described herein is configured to send one or more signals to the controller 90 of the gas turbine engine 10 that are indicative of the particulate level in the engine 10.

Further, as shown in FIG. 5, the sensor 73 may include a circuit board housing 93 configured within the outer housing 76 adjacent to the electrode 86. Thus, the circuit board housing 93 may be configured to house and protect the circuit board 88 therein. The circuit board housing 93 may have any suitable shape. For example, in one embodiment, the circuit board housing 93 may have a shape that generally corresponds to an internal volume of the outer housing 76.

In additional embodiments, as shown in FIGS. 3-5, the electrostatic sensor 73 may also include a sensor cap 99 configured with the second end 83 of the body 79 of the outer housing 76 so as to retain the sensor components, such as the electrode 86 and the amplifier 87, within the outer housing 76. More specifically, as shown, the second end 83 of the body 79 may include a second threaded outer surface 89 configured to receive corresponding threads of an inner surface of the sensor cap 99. In particular embodiments, as shown, the sensor cap 99 may include both an inner threaded surface and/or an outer threaded surface.

Referring still to FIG. 5, the electrostatic sensor(s) 73 may also include one or more insulators 97 or insulation layers. For example, as shown in FIG. 5, the electrostatic sensor(s) 73 may include an insulator 97 between the electrode 86 and the outer housing 76. More specifically, the insulator 97 may be configured with a rear-side of the electrode 86 and may include a hole such that the electrode wire 98 can pass therethrough. It should further be understood that any number of insulators may be employed at any suitable location within the sensor 73.

Referring now to FIGS. 2 and 6, the controller 90 is configured to receive the signals from the sensor(s) 73 from the circuit board 88 that are indicative of the particulate level in the engine 10. More specifically, as shown in FIG. 6, there is illustrated a block diagram of one embodiment of suitable components that may be included in the controller 90 according to the present disclosure. As shown, the controller 90 may include one or more processor(s) 92 and associated memory device(s) 94 configured to perform a variety of computer-implemented functions (e.g., performing the methods, steps, calculations and the like and storing relevant data as disclosed herein). Additionally, the controller 90 may also include a communications module 95 to facilitate communications between the controller 90 and the electrostatic sensor(s) 73. Further, the communications module 95 may include a sensor interface 96 (e.g., one or more analog-to-digital converters) to permit signals transmitted from the sensor(s) 73 to be converted into signals that can be understood and processed by the processor(s) 92. It should be appreciated that the sensor(s) 73 may be communicatively coupled to the communications module 95 using any suitable means. For example, as shown in FIG. 6, the sensors 73 are coupled to the sensor interface 96 via a wired connection. However, in other embodiments, the sensors 73 may be coupled to the sensor interface 96 via a wireless connection, such as by using any suitable wireless communications protocol known in the art. As such, the processor(s) 92 may be configured to receive one or more signals from the sensors 73.

As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 92 may generally include memory element(s) including, but not limited to, computer readable medium (e.g., random access memory (RAM)), computer readable non-volatile medium (e.g., a flash memory), cloud storage, a floppy disk, a compact disc-read only memory (CD-ROM), a magneto-optical disk (MOD), a digital versatile disc (DVD) and/or other suitable memory elements. Such memory device(s) 94 may generally be configured to store suitable computer-readable instructions that, when implemented by the processor(s) 92, configure the controller 90 to perform various functions of the gas turbine engine 10.

Referring now to FIG. 7, a flow diagram of one embodiment of a method 100 for detecting dust or debris in a gas turbine engine 10, e.g. an aircraft engine, is illustrated. As shown at 102, the method 100 includes providing an integrated electrostatic sensor (e.g. sensor 73) in one or more locations of the gas turbine engine 10, such as those illustrated in FIG. 2. Thus, as shown at 104, the method 100 includes mounting the sensing face 85 of each sensor 73 in a particulate flow path at the one or more locations. In addition, as shown at 106, the method 100 includes determining, via the amplifier 87 of each sensor 73, a particulate level of the gas turbine engine 10 as a function of the electron movement. As shown at 108, the method 100 includes generating, via the circuit board 88 configured within the outer housing 76, one or more signals indicative of the particulate level.

In one embodiment, the method 100 may also include sending, via the circuit board 86 of the each of the electrostatic sensors 73, 75, the signal(s) to the controller 90 of the gas turbine engine 10. As such, the sensors 73 described herein provide real-time, accurate particulate level data to a user.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An integrated electrostatic sensor for detecting dust or debris in an engine, the sensor comprising:
    an outer housing comprising a body having a first end and a second end, the first end comprising a sensing face and configured for securing the sensor to the engine;
    an electrode configured within the outer housing adjacent to the sensing face, wherein the electrode comprises an impedance of greater than about 1 G-Ohm, the electrode comprising a plurality of electrons configured to move as charged particles within the engine flow past the sensing face;
    an amplifier configured with the electrode, wherein the amplifier comprises a leakage current of from about 1 femtoampere to about 5 femtoampere and an operating temperature range of from about 100 degrees Celsius to about 250 degrees Celsius, the amplifier configured to detect a particulate level of the engine as a function of the electron movement; and
    a circuit board configured within the outer housing and electrically coupled to the amplifier, the circuit board configured to send one or more signals to a controller of the engine indicative of the particulate level.

2. The sensor of claim 1, wherein the first end comprises a first threaded outer surface configured for securing the sensor in a mounting location of the engine.

3. The sensor of claim 1, wherein the body of the outer housing comprises a predetermined shape configured to fit in an existing location of the engine.

4. The sensor of claim 3, wherein the existing location comprises at least one of a borescope port, a wash water port, a compressor inlet, a booster inlet, or a turbine inlet of the engine.

5. The sensor of claim 3, wherein the predetermined shape of the body of the outer housing comprises a generally cylindrical shape.

6. The sensor of claim 1, further comprising a sensor cap configured with the second end of the body of the outer housing so as to retain the electrode and the amplifier within the outer housing.

7. The sensor of claim 6, wherein the second end comprises a second threaded outer surface configured to receive the sensor cap, the sensor cap comprising at least one of an inner threaded surface or an outer threaded surface.

8. The sensor of claim 1, further comprising an electrode housing configured within the outer housing adjacent to the sensing face, the electrode housing configured to house the electrode, the electrode electrically coupled to the circuit board via an insulated wire.

9. The sensor of claim 1, further comprising a circuit board housing configured within the outer housing adjacent to the electrode, the circuit board housing configured to house the circuit board therein.

10. The sensor of claim 1, further comprising an insulator configured between the electrode and the outer housing.

11. The sensor of claim 1, wherein the engine comprises at least one of an aircraft engine, an industrial engine, a power generation engine, a land-based engine, or a marine engine.

12. An electrostatic sensor system for an engine, the sensor system comprising:
    one or more integrated electrostatic sensors for detecting dust or debris in the engine, each of the electrostatic sensors comprising:
        an outer housing comprising a body having a first end and a second end, the first end comprising a sensing face and configured for securing the sensor to the engine,
        an electrode configured within the outer housing adjacent to the sensing face, wherein the electrode comprises an impedance of greater than about 1 G-Ohm, the electrode comprising a plurality of electrons configured to move as charged particles within the engine flow past the sensing face,
        an amplifier configured with the electrode, wherein the amplifier comprises a leakage current of from about 1 femtoampere to about 5 femtoampere and an operating temperature range of from about 100 degrees Celsius to about 250 degrees Celsius, the amplifier configured to detect a particulate level of the engine as a function of the electron movement, and
        a circuit board configured within the outer housing and electrically coupled to the amplifier; and
    a controller electrically coupled to the circuit board so as to receive one or more signals therefrom that are indicative of the particulate level.

13. The sensor system of claim 12, wherein the first end comprises a first threaded outer surface configured for securing the sensor in a mounting location of the engine.

14. The sensor system of claim 12, wherein the body of the outer housing comprises a predetermined shape configured to fit in an existing location of the engine, wherein the predetermined shape of the body of the outer housing comprises a generally cylindrical shape, wherein the existing location comprises at least one of a borescope port, a wash water port, a compressor inlet, a booster inlet, or a turbine inlet of the engine.

15. The sensor system of claim 12, further comprising:
    an electrode housing configured within the outer housing adjacent to the sensor face, the electrode housing configured to house the electrode, the electrode electrically coupled to the circuit board via an insulated wire, and
    a circuit board housing configured within the outer housing adjacent to the electrode, the circuit board housing configured to house the circuit board therein.

16. A method for detecting dust or debris in an engine, the method comprising:
    providing an integrated electrostatic sensor in one or more locations of the engine, each of the electrostatic sensors including an outer housing with a first end having a sensing face, the first end configured for securing the sensor to the engine, each of the electrostatic sensors also having an internal electrode and amplifier housed within the outer housing, the electrode adjacent to the sensing face and having a plurality of electrons configured to move as charged particles within the engine flow past the sensing face, wherein the electrode comprises an impedance of greater than about 1 G-Ohm;

mounting the sensing face of each sensor in a particulate flow path at the one or more locations;

determining, via the amplifier of each sensor, a particulate level of the engine as a function of the electron movement, wherein the amplifier comprises a leakage current of from about 1 femtoampere to about 5 femtoampere and an operating temperature range of from about 100 degrees Celsius to about 250 degrees Celsius; and generating, via a circuit board configured within the outer housing, one or more signals indicative of the particulate level.

17. The method of claim 16, further comprising sending, via circuit board of the each of the electrostatic sensors, the one or more signals to a controller of the engine.

* * * * *